(12) United States Patent
Jung et al.

(10) Patent No.: US 10,016,469 B2
(45) Date of Patent: Jul. 10, 2018

(54) COMPOSITION COMPRISING ANTIFUNGAL AGENTS FOR TREATING VULVOVAGINITIS AND VAGINOSIS

(71) Applicant: Two Lines Co., Ltd., Gwangju (KR)

(72) Inventors: Chong hyun Jung, Gwangju (KR); Nam Woong Yang, Gwangju (KR)

(73) Assignee: Two Lines Co., Ltd., Gwangju (KR)

(*) Notice: Subject to any disclaimer, the term of this patent is extended or adjusted under 35 U.S.C. 154(b) by 0 days.

(21) Appl. No.: 15/214,470

(22) Filed: Jul. 20, 2016

(65) Prior Publication Data

US 2017/0165304 A1 Jun. 15, 2017

(30) Foreign Application Priority Data

May 26, 2015 (KR) .................. 10-2015-0073193

(51) Int. Cl.
| | | |
|---|---|---|
| *A61K 35/747* | (2015.01) | |
| *A61K 35/74* | (2015.01) | |
| *A61K 47/12* | (2006.01) | |
| *A61K 47/02* | (2006.01) | |
| *A61K 35/00* | (2006.01) | |

(52) U.S. Cl.
CPC ............ *A61K 35/747* (2013.01); *A61K 35/74* (2013.01); *A61K 47/02* (2013.01); *A61K 47/12* (2013.01); *A61K 2035/11* (2013.01)

(58) Field of Classification Search
CPC .................................. C12R 1/225; C12R 1/01
See application file for complete search history.

(56) References Cited

U.S. PATENT DOCUMENTS

| | | |
|---|---|---|
| 6,093,394 A | 7/2000 | Chrisope |
| 2002/0094328 A1 | 7/2002 | De Simone |
| 2005/0186255 A1* | 8/2005 | Rizvi .................. A61K 9/0034 424/443 |
| 2014/0065115 A1 | 3/2014 | Mogna et al. |

FOREIGN PATENT DOCUMENTS

| | | |
|---|---|---|
| KR | 10-2001-0006273 A | 1/2001 |
| KR | 10-2002-0020544 A | 3/2002 |
| KR | 10-2002-0033643 A | 5/2002 |
| KR | 10-2004-0012779 A | 2/2004 |
| KR | 10-2007-0098116 A | 10/2007 |
| KR | 10-2014-0029392 A | 3/2014 |

OTHER PUBLICATIONS

Sihn et al., J of Bacteriology and Virology, 2014, vol. 44, No. 3, p. 244-251.*
Antonio M, Petrina M, Meyn L, Hillier S. Lactobacillus crispatus colonisation reduces risk of bacterial vaginosis (BV) acquisition. Sex Transmit Infect 2011;87:A304-5.
Yang NW, Sin SH, Chang JS. Diagnosis of bacterial vaginosis with relation to isolation of Gardnerella vaginalis. J Bactriol 57-18 May 26, 2015 Viral 2002;32:109-14.
Yang NW, Kim JM, Choi GJ, Jang SJ. Development and evaluation of the quick anaero-system-A new disposable anaerobic culture system. Korean J Lab Med 2010;30:133-7.

* cited by examiner

*Primary Examiner* — Ruth A Davis
(74) *Attorney, Agent, or Firm* — Revolution IP, PLLC (57) ABSTRACT

Disclosed is a method of treating vaginosis with a composition having *Steroidobacter denitrificans* YH1 (KCTC18345P) and *Lactobacillus crispatus* YH2 (KCTC18346P) strains, wherein the composition further includes at least one buffer selected from the group consisting of sodium phosphate monobasic, sodium phosphate dibasic, sodium phosphate tribasic, citric acid, sodium citrate, phosphoric acid, hydrochloric acid, sodium hydroxide, sodium pyrophosphate, and pyrophosphate.

7 Claims, 9 Drawing Sheets

FIG. 6B

SEQUENCE LISTING

<160> NUMBER OF SEQ ID NOS: 2

<210> SEQ ID NO 1
<211> LENGTH: 879
<212> TYPE: DNA
<213> ORGANISM: Steroidobacter denitrificans YH1

<400> SEQUENCE: 1

```
acaggtgtag caatacatgc tgacgagcgg cgaacgggtg agtaatgctt cggaatctac      60
cttatggtgg ggaataacta gccgaaaggt tagctaatac cgcatacgtc ctacgggaga     120
aagcagggga tcgcaagacc ttgcgccaaa agatgagccg aagtcggatt agctagttgg     180
tagggtaacg gcctaccaag gcgacgatcc gtagctggtc tgagaggacg accagccaca     240
```

```
ctgggactga gacacggccc agactcctac gggaggcagc agtggggaat attggacaat    300
gggggaaacc ctgatccagc gacgccgcgt gtgtgaagaa ggcctgcggg ttgtaaagca    360
cttttagtgg ggatgaaatg tgcagggcta acacctctgc attttgacct aacccacaga    420
aaaagcaccg gctaactctg tgccagcagc cgcggtaata cagagggtgc aagcgttaat    480
cggaattact gggcgtaaag cgtgcgtaga cggttacata agtcgggtgt gaaagccccg    540
ggctcaacct gggaattgca ttcgagactg cgtagctagg gtgcggaaga gggaagcgga    600
atttccggtg tagcggtgaa atgcgtagat atcggaagga acaccagtgg cgaaagcggc    660
ttcctggtcc agcaccgacg ttcaggcacg aaagcgtggg gagcaaacag gattagatac    720
cctggtagtc cacgccataa acgatgagaa ctagacgttg aaggggtaag ccctccagtg    780
tcgtagctaa cgcgctaagt tctccgcctg gggagtacgg ccgcaaggtt gaaactcaaa    840
ggaattgacg gggacccgca caagcggtgg agcatgtgg                           879

<210> SEQ ID NO 2
<211> LENGTH: 956
<212> TYPE: DNA
<213> ORGANISM: Lactobacillus crispatus YH2

<400> SEQUENCE: 2
agtcgagcga gcggaactaa cagatttact tcggtaatga cgttaggaaa gcgagcggcg     60
gatgggtgag taacacgtgg ggaacctgcc ccatagtctg ggataccact tggaaacagg    120
tgctaatacc ggataagaaa gcagatcgca tgatcagctt ttaaaaggcg gcgtaagctg    180
tcgctatggg atggccccgc ggtgcattag ctagttggta aggtaaaggc ttaccaaggc    240
gatgatgcat agccgagttg agagactgat cggccacatt gggactgaga cacggcccaa    300
actcctacgg gaggcagcag tagggaatct tccacaatgg acgcaagtct gatggagcaa    360
cgccgcgtga gtgaagaagg ttttcggatc gtaaagctct gttgttggtg aagaaggata    420
gaggtagtaa ctggccttta tttgacggta atcaaccaga aagtcacggc taactacgtg    480
ccagcagccg cggtaatacg taggtggcaa gcgttgtccg gatttattgg gcgtaaagcg    540
agcgcaggcg gaagaataag tctgatgtga aagccctcgg cttaaccgag gaactgcatc    600
ggaaactgtt tttcttgagt gcagaagagg agagtggaac tccatgtgta gcggtggaat    660
gcgtagatat atggaagaac accagtggcg aaggcggctc tctggtctgc aactgacgct    720
gaggctcgaa agcatgggta gcgaacagga ttagataccc tggtagtcca tgccgtaaac    780
gatgagtgct aagtgttggg aggtttccgc ctctcagtgc tgcagctaac gcattaagca    840
ctccgcctgg ggagtacgac cgcaaggttg aaactcaaag gaattgacgg gggcccgcac    900
aagcggtgga gcatgtggtt taattcgaag caacgcgaag aaccttacca ggtctt       956
```

COMPOSITION COMPRISING ANTIFUNGAL AGENTS FOR TREATING VULVOVAGINITIS AND VAGINOSIS

CROSS REFERENCE TO PRIOR APPLICATIONS

This application claims priority to Korean Patent Application No. 10-2015-0073193 filed on May 26, 2015, which is hereby incorporated by reference in its entirety.

BACKGROUND

1. Field of the Invention

The present invention relates to a composition for treating vaginosis, and more particularly, to a composition for treating vaginosis including *Steroidobacter denitrificans* YH1 (KCTC18345P) and *Lactobacillus crispatus* YH2 (KCTC18346P) strains.

2. Discussion of Related Art

Bacterial vaginosis, which causes milky white homogeneous leukorrhea with an unpleasant odor, as a main symptom, is the most common vaginal disease among sexually active women of childbearing age (Non-Patent Document 1). The unpleasant odor of bacterial vaginosis occurs when normal flora, such as lactic acid-generating bacteria, in the vagina are replaced with obligate anaerobes (*Bacteroides* spp., *Mobiluncus* spp., *Peptococcus* spp., *Peptostreptococcus* spp., *Prevotella* spp.) while the number of facultative anaerobes, such as *Gardnerella vaginalis*, increases (Non-Patent Document 1).

As currently used treatments, there are a method of killing all bacteria in the vagina with a metronidazole or clindamycin vaginal suppository or an iodine based germicide, as an antibiotic to which anaerobic bacteria are sensitive, a method of lowering the pH of the interior of the vagina with a 1% lactic acid solution or an acetic acid solution such that a pH, i.e., about 4.5, of the interior of the vagina of healthy women is maintained and thus the growth of bacteria causing bacterial vaginosis is inhibited and an increase in the number of normal flora is induced, or about 40 folk remedies including the use of mugwort and plantains. However, bacterial vaginosis frequently recurs and a complete remedy therefor has yet to be found.

Commonly used antibiotics kill even beneficial normal flora while selectively killing causative bacteria of bacterial vaginosis, which causes frequent recurrence. In addition, vaginal cleansers containing an iodine compound, such as gynobetadine, also kill all bacteria in the vagina. Accordingly, temporary effects are exhibited, but the remaining bacteria re-proliferate, thereby leading to recurrence of an illness. Although folk remedies, such as a vinegar remedy, a lactic acid remedy, a smoked mugwort remedy, are present, none guarantees complete recovery.

Accordingly, research into a new probiotic remedy for inhibiting causative bacteria of bacterial vaginosis by directly injecting lactic acid bacteria into the vagina and treatment using the same has been conducted (Non-Patent Document 2). However, this remedy also exhibits a slight therapeutic effect and has not been commercialized.

SUMMARY

The present invention is directed to a lactic acid bacteria-containing composition for treating vaginosis, the lactic acid bacteria-containing composition exhibiting an effective therapeutic effect for bacterial vaginosis in women.

According to an aspect of the present invention, there is provided a composition for treating vaginosis including *Steroidobacter denitrificans* YH1 (KCTC18345P) and *Lactobacillus crispatus* YH2 (KCTC18346P) strains.

According to an example of the present invention, the composition may further include at least one buffer selected from the group consisting of sodium phosphate monobasic, sodium phosphate dibasic, sodium phosphate tribasic, citric acid, sodium citrate, phosphoric acid, hydrochloric acid, sodium hydroxide, sodium pyrophosphate, and pyrophosphate.

According to an example of the present invention, the composition may further include sodium phosphate tribasic and citric acid as a buffer.

According to an example of the present invention, the composition may include the buffer at an amount of 0.01 to 10% (WN).

According to an example of the present invention, the pH of the composition is 2 to 7.

According to an example of the present invention, a ratio of the number of *Lactobacillus crispatus* (*Lactobacillus crispatus*) YH2 (KCTC18346P) to the number of the *Steroidobacter denitrificans* YH1 (KCTC18345P) may be 1:100 to 100:1.

According to an example of the present invention, the composition may reduce and/or remove the existence and/or activity of pathogens selected from the group including *Gardnerella vaginalis, Trichomonas vaginalis, Neisseria gonorrhoeae, Streptococcus, Staphylococcus, Escherichia coli, Peptostreptococcus* spp., *Mobiluncus* spp., *Bacteroides* spp., *Prevotella* spp., *Peptococcus* spp., and *Mycoplasma hominis*.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

To accomplish the aforementioned objects, the present invention provides a composition for treating vaginosis including *Steroidobacter denitrificans* YH1 (KCTC18345P) and *Lactobacillus crispatus* YH2 (KCTC18346P) strains. Hereinafter, the present invention is described in more detail with reference to the accompanying drawings.

*Steroidobacter denitrificans* (hereinafter referred to as *S. denitrificans*) YH1 (KCTC18345P) was isolated from the vagina of a healthy woman and identified. The 16S RNA sequence thereof is the same as set forth in Sequence ID NO. 1.

*Lactobacillus crispatus* (hereinafter referred to as *L. crispatus*) YH2 (KCTC18346P) was isolated from the vagina of a healthy woman and identified. 16S RNA sequence thereof is the same as set forth in Sequence ID NO. 2.

The composition of the present invention may include a commonly used buffer. The buffer may be at least one selected from the group consisting of sodium phosphate monobasic, sodium phosphate dibasic, sodium phosphate tribasic, citric acid, sodium citrate, phosphoric acid, hydrochloric acid, sodium hydroxide, sodium pyrophosphate, and pyrophosphate, but the present invention is not limited thereto. In a preferred embodiment, the composition of the present invention may include sodium phosphate tribasic and citric acid. The buffer may be included in an amount of 0.01 to 10% (WN). By using the buffer, an environment suitable for the proliferation of the bacteria of the present invention can be provided.

The composition of the present invention may have a pH that is suitable for the activity of lactic acid bacteria and commonly used. For example, the pH may be 2 to 7, more preferably 4 to 5.

The strains included in the composition of the present invention may be included in an effective amount which exhibits the activity thereof. In an embodiment, 1 ml of the composition may include $1^1$ to $9^{20}$ bacteria, but, the present invention is not limited thereto. Preferably, 1 ml of the composition includes about $1^3$ to $9^{10}$ bacteria.

When *Steroidobacter denitrificans* (*S. denitrificans*) YH1 (KCTC18345P) and *Lactobacillus crispatus* (*L. crispatus*) YH2 (KCTC18346P) are used together, a ratio of the number of *Lactobacillus crispatus* (*L. crispatus*) YH2 to the number of *Steroidobacter denitrificans* (*S. denitrificans*) YH1 bacteria may be 1:100 to 100:1. More preferably, the ratio may be 1:10 to 10:1.

The composition of the present invention decreases the activity and number of bacteria causing vaginosis. More particularly, the composition may reduce, eliminate, and/or inactivate pathogens selected from the group including *Gardnerella vaginalis*, *Trichomonas vaginalis*, *Neisseria gonorrhoeae*, *Streptococcus*, *Staphylococcus*, *Escherichia coli*, *Peptostreptococcus* spp., *Mobiluncus* spp., *Bacteroides* spp., *Prevotella* spp., *Peptococcus* spp., and *Mycoplasma hominis*.

The strains used in the present invention become main bacteria (normal flora) in the vagina of a patient suffering from bacterial vaginosis and inhibit proliferation of causative bacteria of bacterial vaginosis. In addition, citric acid and sodium phosphate tribasic lower the pH of the interior of the vagina to 4.0-4.5, thereby directly inhibiting the growth of causative bacteria of bacterial vaginosis. Further, citric acid and sodium phosphate tribasic guarantee the survival of the bacteria of the present invention and further increase the pathogen inhibition capability of the bacteria. Accordingly, the present invention can return a bacterial ecosystem in the vagina of a patient suffering from recurrent bacterial or atrophic vaginosis to an original healthy state and greatly lower a recurrence rate of an illness.

Hereinafter, the present invention will be described in more detail with reference to the following examples. The scope of the present invention is not limited to the following examples and covers modifications of the technical spirit substantially equivalent thereto.

Example

1. Obtaining and Culturing Bacteria

Man-Rogosa-Sharpe (MRS) agar (MERCK, Germany) was inoculated with a sample collected from the vagina of a healthy 43 year old woman who was diagnosed as being negative for bacterial vaginosis by applying Amsel's composite clinical criteria (Non-Patent Document 3), as a diagnostic criterion for bacterial vaginosis, and the results of Yang et al. (Non-Patent Document 4), followed by anaerobic culture in a disposable anaerobic culture system (Quick anaero-system, Sindo Co., Korea) for 48 hours under a condition of 5% carbon dioxide (Non-Patent Document 5).

Subsequently, two strains having different shapes and sizes were isolated and subjected to gram staining. As a result, both strains were gram-positive bacilli and the microscopic morphologies thereof were different.

The two strains optimally grew under anaerobic conditions. Although they grew under a condition of 5 to 10% oxygen, a growth rate under this condition was lower than that under anaerobic conditions. Carbon dioxide was not necessary to realize optimal growth of the two strains. When the two strains were refrigerated under a 5% hypoxic condition, the number of the bacteria was decreased after storage for five days and the bacteria were completely eliminated after storage for 12 days. On the other hand, when refrigerated under anaerobic conditions, the number of the bacteria was not decreased. From these results, it can be confirmed that the both bacterial strains grow under anaerobic, aerotolerant, and carbon dioxide-deficient conditions.

2. Molecular Biological Identification of Isolated Bacteria

Figure 1A:
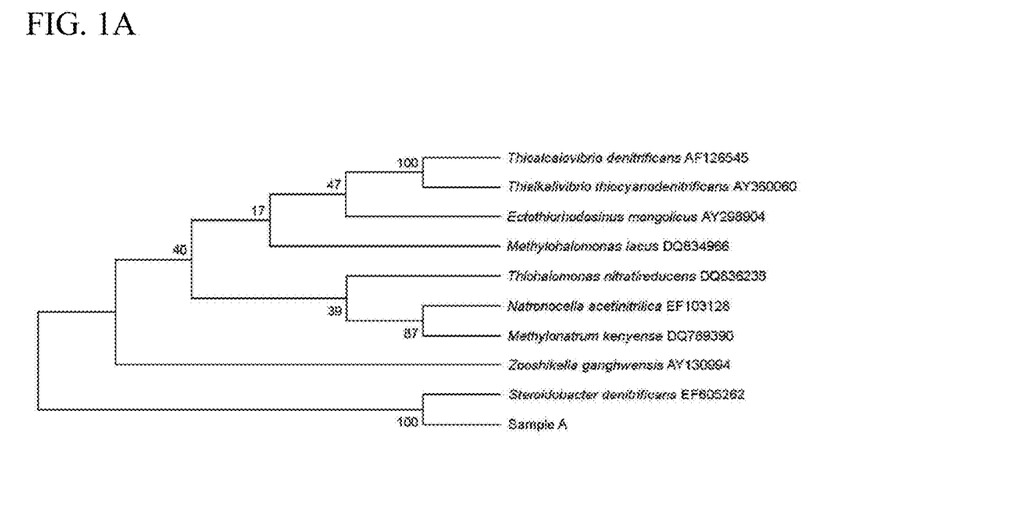
FIG. 1A illustrates a 16S RNA-based unrooted neighbor joining phylogenetic tree of *Steroidobacter denitrificans* YH1, as the strain of the present invention.
Figure 1B:
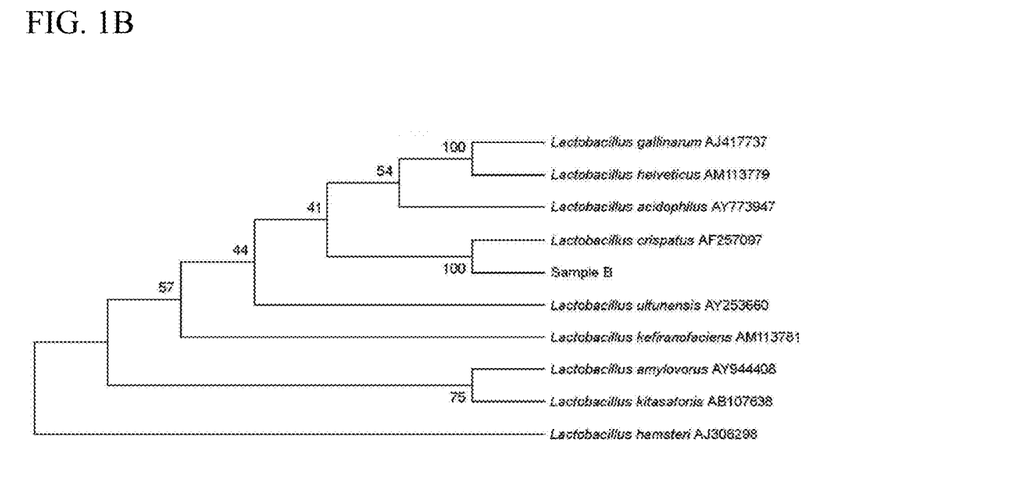
FIG. 1B illustrates a 16S RNA-based unrooted neighbor joining phylogenetic tree of *Lactobacillus crispatus* YH2, as the strain of the present invention.

The two bacterial strains were sent to the Korean Culture Center of Microorganisms (KCCM) under anaerobic conditions and partial 16S rRNA sequencing of each thereof was requested. They were identified as *Steroidobacter denitrifican* and *Lactobacillus crispatus*, respectively (Gene Bank Data homology search results: 99%), (See FIGS. 1A and 1B). Accordingly, the stains were named *Steroidobacter denitrificans* (*S. denitrificans*) YH1 and *Lactobacillus crispatus* (*L. crispatus*) YH2, respectively.

Partial 16S rRNA sequencing of each of the isolated strains was carried out as follows: Chromosomal DNAs of the bacteria were isolated using a Wizard genomic DNA purification kit (Promega, US) and then subjected to PCR amplification with a universal primer, 27F (5'-AGAGTTT-GATCATGGCTCAG-3'), used in 16S rRNA sequencing using a MyCycler Thermal Cycler system (Bio-Rad). Amplified PCR products were purified using the Wizard SV Gel and PCR Clean-Up system (Promega, US). Resultant purified products were subjected to sequence analysis using the ABI PRISM BigDye™ Terminator Cycle Sequencing Kit (Applied Biosystems Co.) by means of the ABI PRISM 3730XL analyzer (96 capillary type). Results were compared with the sequences of the ribosomal DNA of GEN-EBANK using the BLASTN program. Homology between sequences was compared and analyzed using the Clustal X and Mega 6 programs.

As results, 16S RNA sequences of *Steroidobacter denitrificans* (*S. denitrificans*) YH1 were the same as set forth in Sequence ID NO. 1 and 16S RNA sequences of *Lactobacillus crispatus* (*L. crispatus*) YH2 were the same as set forth in Sequence ID NO. 2.

The strains, *Steroidobacter denitrificans* (*S. denitrificans*) YH1 and *Lactobacillus crispatus* (*L. crispatus*) YH2, were respectively deposited as Deposition Nos. KCTC18345P and KCTC18346P with the Korea Research Institute of Bioscience and Biotechnology.

3. Biochemical Description of Isolated Bacteria

The isolated two strains, *Steroidobacter denitrificans* (*S. denitrificans*) YH1 and *Lactobacillus crispatus* (*L. crispatus*) YH2 were subjected to an experiment using the API 50 CHL kit (BIOMETRIUX, France). *S. denitrificans* YH1 was subjected to an additional experiment using the API ZYM kit (BIOMETRIUX, France) to investigate enzyme activity. Both strains were cultured under anaerobic conditions.

As results of the biochemical examination using the API CHL kit, *Steroidobacter denitrificans* (*S. denitrificans*) YH1 hydrolyzed galactose, D-glucose, D-fructose, D-mannose, mannitol, N-acetylglucosamine, esculin, salicine, cellobiose, maltose, lactose, saccharose, trehalose, amidon, and glycogen.

*Lactobacillus crispatus* (*L. crispatus*) YH2 hydrolyzed galactose, D-glucose, D-fructose, D-mannose, N-acetyl glucosamine, esculin, maltose, lactose, saccharose, and glycogen, but did not hydrolyze salicine, cellobiose, trehalose, and amidon (See Table 1).

TABLE 1

| No. | Item | S. denitrificans YH1 | L. crispatus YH2 |
|---|---|---|---|
| 0 | Control | − | − |
| 1 | Glycerol | − | − |
| 2 | Erythritol | − | − |
| 3 | D-arabinose | − | − |
| 4 | L-arabinose | − | − |
| 5 | Ribose | − | − |
| 6 | D-xylose | − | − |
| 7 | L-xylose | − | − |
| 8 | Adonitol | − | − |
| 9 | β-methyl-xyloside | − | − |
| 10 | Galactose | + | + |
| 11 | D-glucose | + | + |
| 12 | D-fructose | + | + |
| 13 | D-mannose | + | + |
| 14 | L-sorbose | − | − |
| 15 | Rhamnose | − | − |
| 16 | Dulcitol | − | − |
| 17 | Inositol | − | − |
| 18 | Mannitol | + | − |
| 19 | Sorbitol | − | − |
| 20 | α-ethyl-D-mannoside | − | − |
| 21 | α-methyl-D-glucoside | − | − |
| 22 | N-acetyl glucosamine | + | + |
| 23 | Amygdaline | − | − |
| 24 | Arbutine | − | − |
| 25 | Esculine | + | + |
| 26 | Salicine | + | − |
| 27 | Cellobiose | + | − |
| 28 | Maltose | + | + |
| 29 | Lactose | + | + |
| 30 | Melibiose | − | − |
| 31 | Saccharose | + | + |
| 32 | Trehalose | + | − |
| 33 | Inuline | − | − |
| 34 | Melezitose | − | − |
| 35 | D-raffinose | − | − |
| 36 | Amidon | + | − |
| 37 | Glycogen | + | + |
| 38 | Xylitol | − | − |
| 39 | β-gentiobiose | − | − |
| 40 | D-turanose | − | − |
| 41 | D-lyxose | − | − |
| 42 | D-tagatose | − | − |
| 43 | D-fucose | − | − |
| 44 | L-fucose | − | − |
| 45 | D-arabitol | − | − |
| 46 | L-arabitol | − | − |
| 47 | Gluconate | − | − |
| 48 | 2-keto-gluconate | − | − |
| 49 | 5-keto-gluconate | − | − |

4. Growth Inhibition Effects of Strains of the Present Invention for Causative Bacteria of Vaginosis (1) Streak Plate Experiment and Result A human red blood cell solution was prepared as follows: A saline solution was added to concentrated red blood cells, followed by washing through centrifugation three times at 3,000 rpm in a refrigerated centrifuge (Vision Scientific Co., VS-21SR, Korea). Distilled water was added to a resultant red blood cell solution, from which a supernatant was removed, thereby reducing the amount of human whole blood. A resultant red blood cell solution was contained in a flexible plastic container and frozen in a −80° C. freezer for 30 minutes. The frozen solution was removed from the freezer and immediately thawed. This process was repeated three times. The thawed red blood cell solution was diluted 2.5× with distilled water and then centrifuged at 15,000 rpm by means of a refrigerated centrifuge. Only supernatant was collected and sterile-filtered through a disposable 0.45 μm Millipore filter, followed by storage in a −80° C. freezer. As required, the frozen supernatant was thawed and used.

An experiment for *Gardnerella vaginalis* (*G. vaginalis*, ATCC 14018) was carried out as follows: Casman agar base (BBL, US) was equivalently mixed with MRS agar (Merck, Germany) and a human red blood cell solution was added thereto in a ratio of 5%, which was abbreviated "CMB medium." *Gardnerella vaginalis* (*G. vaginalis*) was cultured in Casman broth including a human red blood cell solution in an amount of 5% under 5% carbon dioxide and anaerobic conditions for 48 hours. A resultant solution including the bacteria was diluted 1,000 fold with a saline solution. The diluted solution was collected with a cotton swab and smeared on the CMB agar. *Steroidobacter denitrificans* (*S. denitrificans*) YH1 and *Lactobacillus crispatus* (*L. crispatus*) YH2 anaerobically cultured for 24 hours in the MRS liquid medium were respectively diluted 100 fold with a saline solution and 10 μl therefrom was taken. Subsequently, each of *Steroidobacter denitrificans* (*S. denitrificans*) YH1 and *Lactobacillus crispatus* (*L. crispatus*) YH2 was added dropwise onto the center of the CMB agar, on which *Gardnerella vaginalis* (*G. vaginalis*) was smeared. Resultant plates were cultured under a 5% carbon dioxide and anaerobic conditions for 48 hours. After culturing, the diameters (mm) of growth inhibition zones around the probiotics were measured.

Experiments for *Bacteroides fragilis* (*B. fragilis*, ATCC 25285), *Mobiluncus mulieris* (*M. mulieris*, ATCC 35239), and *Peptostreptococcus asaccharolyticus* (*P. asaccharolyticus*, KCTC 3321) were carried out as follows: Wilkins-Chalgren agar (Wilkins-Chalgren agar, DIFCO, US) was equivalently mixed with MRS agar, which was abbreviated "WCM medium." Each of the three strains anaerobically cultured in Wilkins-Chalgren Anaerobe Broth (OXOID, England) for 48 hours was diluted 2,000 fold with a saline solution and was collected with a cotton swab, followed by smearing on a WCM agar. Each of *Steroidobacter denitrificans* (*S. denitrificans*) YH1 and *Lactobacillus crispatus* (*L. crispatus*) YH2 was diluted 100 fold with a saline solution and 10 μl thereof was collected, followed by adding dropwise on the center of a WCM agar, on which each of the three strains was smeared. Resultant plates were cultured under 5% carbon dioxide and anaerobic conditions for 48 hours. After culturing, the diameters (mm) of growth inhibition zones around the probiotics were measured.

Figure 2:
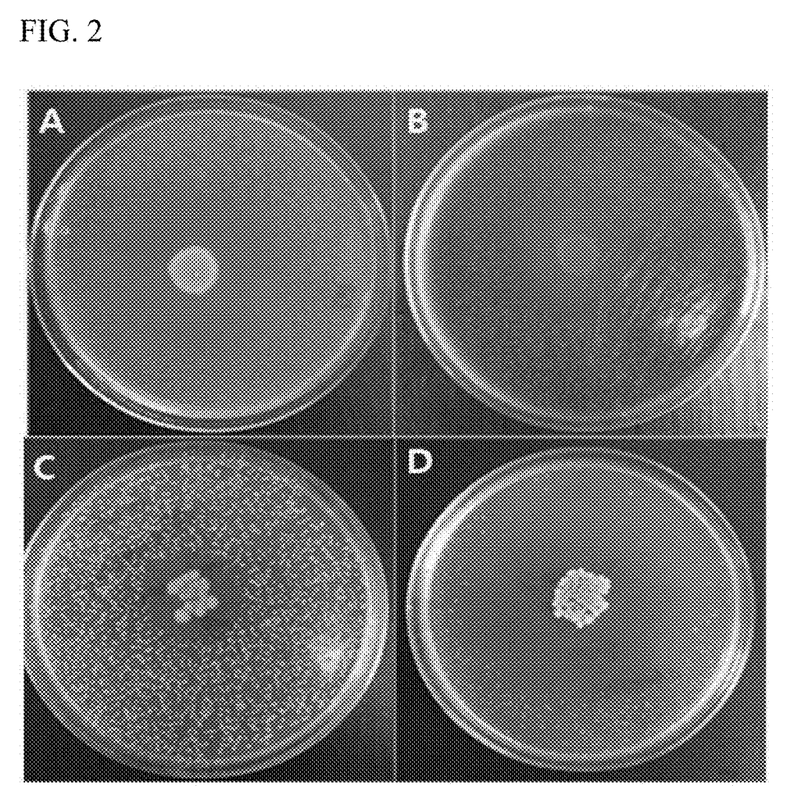
FIG. 2 illustrates proliferation inhibition effects of *Steroidobacter denitrificans* YH1, as the strain of the present invention, against causative bacteria of vaginosis. A: *Bacteroides fragilis* (*B. fragilis*); B: *Gardnerella vaginalis* (*G. vaginalis*); C: *Mobiluncus mulieris* (*M. mulieris*); and D: *Peptostreptococcus asaccharolyticus* (*P. asaccharolyticus*)
Figure 3:
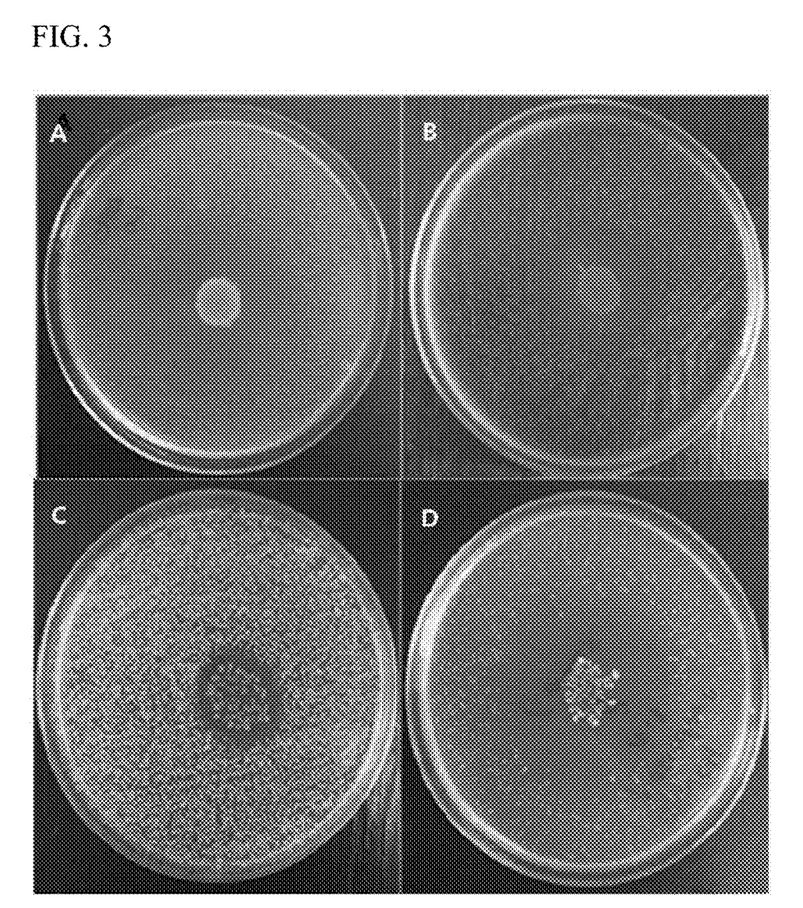
FIG. 3 illustrates proliferation inhibition effects of *Lactobacillus crispatus* YH2, as the strain of the present invention, against causative bacteria of vaginosis. A: *Bacteroides fragilis* (*B. fragilis*); B: *Gardnerella vaginalis* (*G. vaginalis*); C: *Mobiluncus mulieris* (*M. mulieris*); and D: *Peptostreptococcus asaccharolyticus* (*P. asaccharolyticus*)

Three plates were used per strain. Experimental results are illustrated in FIGS. 2 and 3. An average diameter of growth inhibition zones of the three plates is illustrated and summarized in Table 2 below (Unit: mm, disclosed values are averages of values measured three times).

TABLE 2

|  | B. fragilis | G. vaginalis | M. mulieris | P. asaccharolyticus |
|---|---|---|---|---|
| S. denitrificans YH1 | 35 | 35 | 25 | 60 |
| L. crispatus YH2 | 25 | 30 | 20 | 40 |

*Steroidobacter denitrificans* (*S. denitrificans*) YH1 was subjected to an enzyme activity test using an API ZYM kit. By this test, alkaline phosphatase, trypsin, β-galactosidase, α-glucosidase, and β-glucosidase activity were exhibited (See Table 3).

TABLE 3

| No. | Items | Results |
|---|---|---|
| 0 | Control | − |
| 1 | Alkaline phosphatase | + |
| 2 | Esterase (C4) | − |
| 3 | Esterase lipase (C8) | − |
| 4 | Lipase (C14) | − |
| 5 | Leucine arylamidase | − |
| 6 | Valine arylamidase | − |
| 7 | Crystine arylamidase | − |
| 8 | Trypsin | + |
| 9 | α-chymotrypsin | − |
| 10 | Acid phosphatase | − |
| 11 | Naphthol-AS-B1-phosphohydrolase | − |
| 12 | α-galactosidase | − |
| 13 | β-galactosidase | + |
| 14 | β-glucuronidase | − |
| 15 | α-glucosidase | + |
| 16 | β-glucosidase | + |
| 17 | N-acetyl-β-glucosaminidase | − |
| 18 | α-mannosidase | − |
| 19 | α-fucosidase | − |

(2) Mixed Solution Culture Experiment and Results

Using two CMB liquid media, 100 μl of an undiluted medium of *Gardnerella vaginalis* (*G. vaginalis*, ATCC 14018) was mixed with 20 μl of an undiluted medium of each of *Steroidobacter denitrificans* (*S. denitrificans*) YH1 and *Lactobacillus crispatus* (*L. crispatus*) YH2, followed by anaerobically culturing for 48 hours. 100 μl from each of the media was collected with an auto-pipette. The collected medium was streaked on each of the Casman's blood agar for isolating *G. vaginalis* and the MRS agar for isolating each of *Steroidobacter denitrificans* (*S. denitrificans*) YH1 and *Lactobacillus crispatus* (*L. crispatus*) YH2. Resultant plates were anaerobically cultured for 48 hours under 5% carbon dioxide.

*Gardnerella vaginalis* (*G. vaginalis*) was mixed with *Steroidobacter denitrificans* (*S. denitrificans*) YH1 and cultured in a CMB liquid medium. Subsequently, *Gardnerella vaginalis* (*G. vaginalis*) was isolated from the Casman's blood agar (Casman's blood agar) by a streak plate method. However, colonies from *Gardnerella vaginalis* (*G. vaginalis*) were not isolated at all. *Steroidobacter denitrificans* (*S. denitrificans*) YH1 was cultured in the MRS agar in bulk.

*Gardnerella vaginalis* (*G. vaginalis*) was mixed with *Lactobacillus crispatus* (*L. crispatus*) YH2 and cultured in a CMB liquid medium. The strain was isolated according to the aforementioned methods. As described above, colonies of *Gardnerella vaginalis* (*G. vaginalis*) were not isolated at all and *Lactobacillus crispatus* (*L. crispatus*) YH2 was cultured in the MRS agar in bulk.

5. Growth Inhibition Effects of a Mixture of Citric Acid and Sodium Phosphate Tribasic on Causative Bacteria of Vaginosis (1) Inhibition of Growth of *Gardnerella vaginalis* (*G. vaginalis*)

A basal liquid medium was prepared by adding a human red blood cell solution in a ratio of 5% to Wilkins-Chalgren anaerobe broth. A medium for each experiment was prepared as follows.

TABLE 4

|  | Control (basal medium) | WCCT-1 | WCCT-2 | WCCT-3 |
|---|---|---|---|---|
| Citric acid monohydrate | — | 0.25% | 0.5% | 1.0% |
| Trisodium phosphate 12hydrate | — | 0.55% | 0.8% | 2.6% |
| pH | 6.92 | 6.27 | 6.27 | 6.27 |

Each of the media was aliquoted in an amount of 5 ml into a screw cap tube. 100 μl of a medium, which was sterilized and anaerobically cultured for 24 hours, for *Gardnerella* vaginalis (G. vaginalis, ATCC 14018), was added to the screw cap tubes, followed by anaerobically culturing. At 24 and 48 hours after culturing, the solutions containing the bacteria were serially diluted 10 fold with a saline solution. 100 μl from each diluent was collected and spread on three plates prepared by adding blood to Columbia agar base (Merck, Germany). According to a spread plate method, resultant plates were cultured for 48 hours, the numbers of colonies formed were calculated, and average values were determined.

Figure 4:
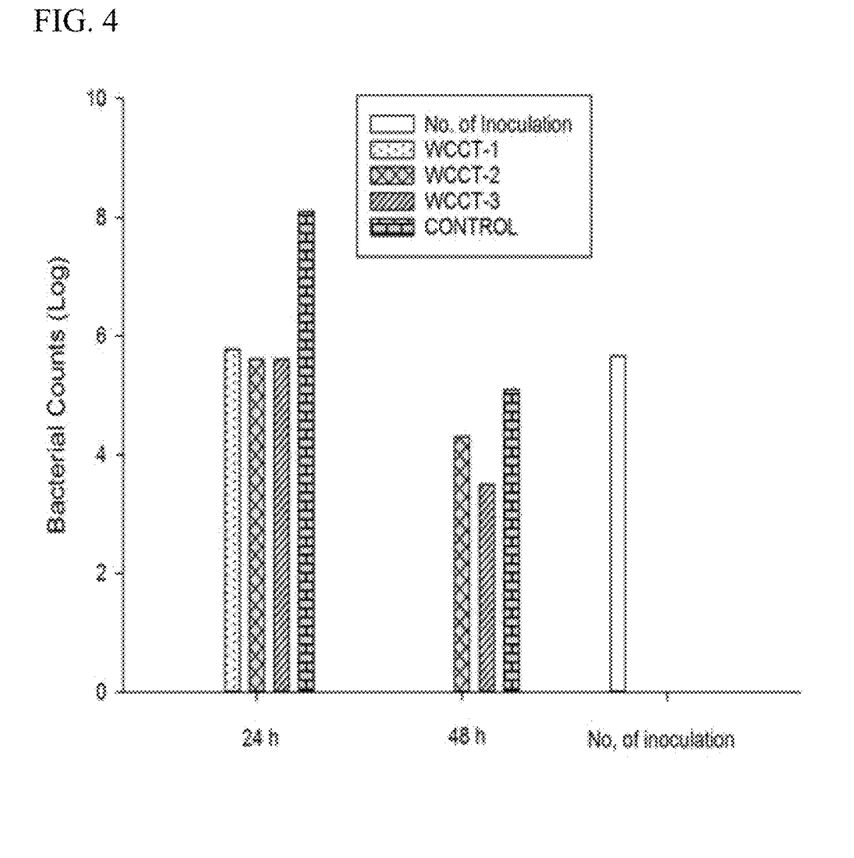
FIG. 4 illustrates a proliferation inhibition experiment result of *Gardnerella vaginalis* (*G. vaginalis*) with a mixed solution including citric acid and sodium phosphate tribasic.

Experimental results are shown in Table 5 and FIG. 4. The number of colonies at an early culture stage is $2.3\times10^6$/ml.

The three strains were as follows: Bacteroides fragilis (B. fragilis, ATCC 25285), Mobiluncus mulieris (M. mulieris, ATCC 35239), and Peptostreptococcus asaccharolyticus (P. asaccharolyticus, KCTC 3321).

At 24 and 48 hours after culturing, the media were respectively spread on Wilkins-Chalgren agar according to the spread plate method as in the case of Gardnerella vaginalis (G. vaginalis).

Figure 5A:
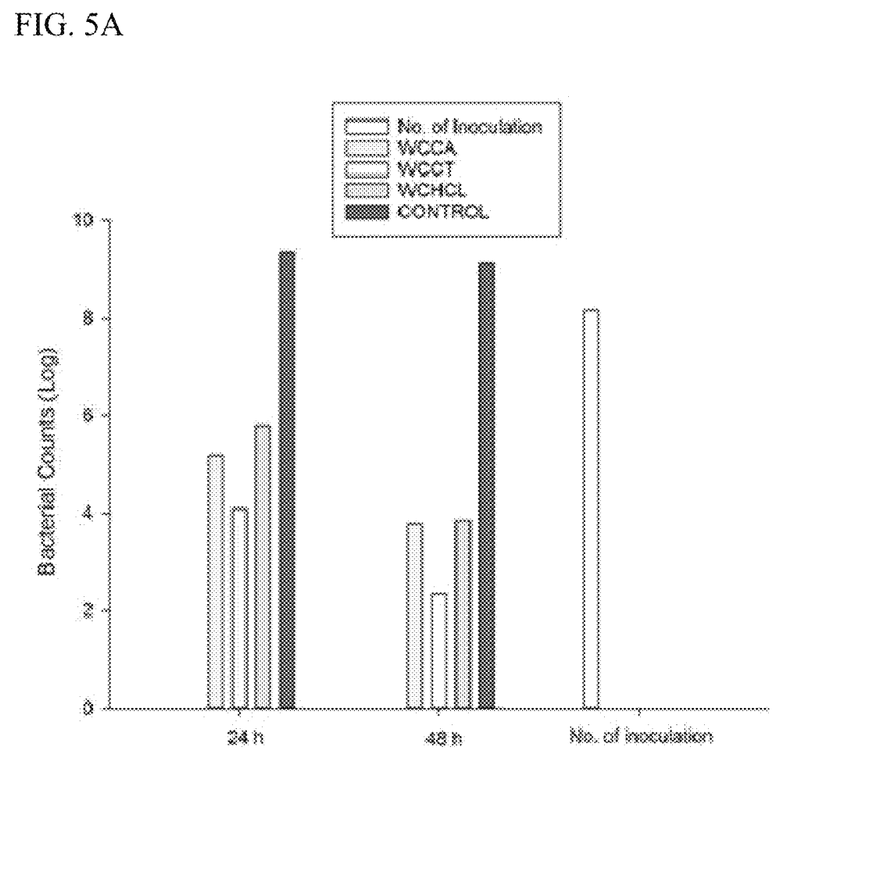
FIG. 5A illustrates a proliferation inhibition experiment result of *Bacteroides fragilis* (*B. fragilis*) with a mixed solution including citric acid and sodium phosphate tribasic.
Figure 5B:
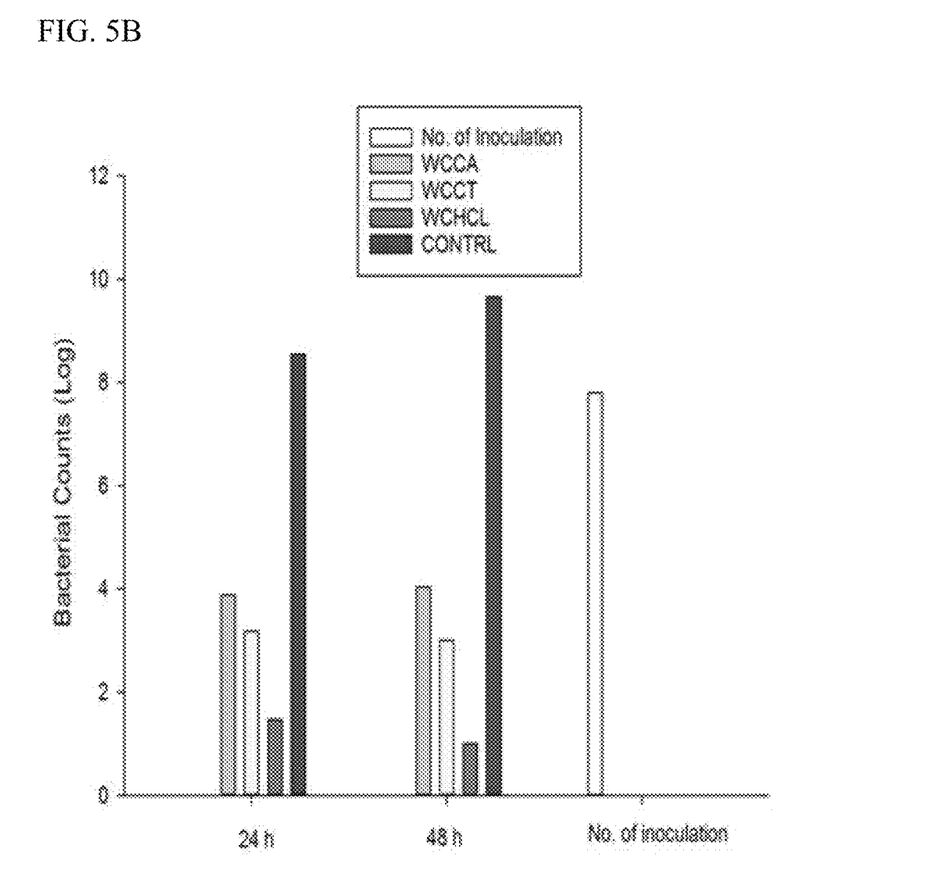
FIG. 5B illustrates a proliferation inhibition experiment result of *Mobiluncus mulieris* (*M. mulieris*) with a mixed solution including citric acid and sodium phosphate tribasic.
Figure 5C:
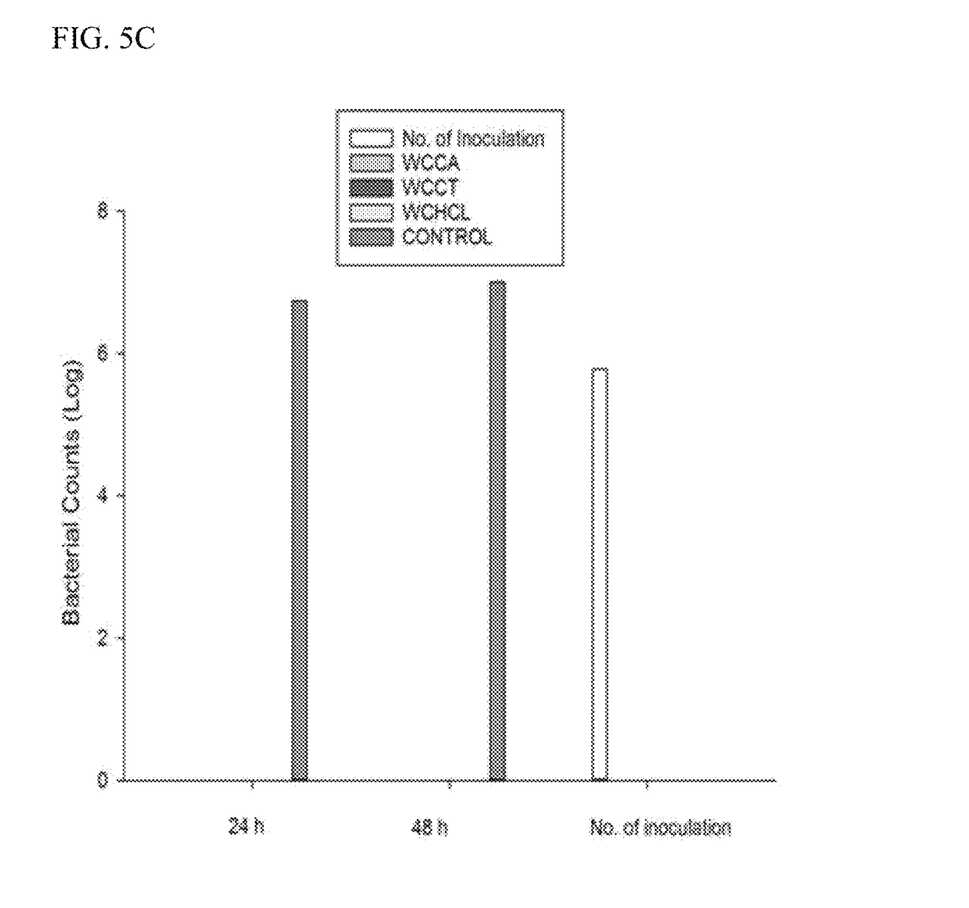
FIG. 5C illustrates a proliferation inhibition experiment result of *Peptostreptococcus asaccharolyticus* (*P. asaccharolyticus*) with a mixed solution including citric acid and sodium phosphate tribasic.

Experimental results are shown in Table 7 and FIG. 5. (Unit: /ml)

TABLE 7

| | Stain | | | | | |
| --- | --- | --- | --- | --- | --- | --- |
| | B. fragils | | M. mulieris | | P. asaccharolyticus | |
| Medium | 24 hours after culture | 48 hours after culture | 24 hours after culture | 48 hours after culture | 24 hours after culture | 48 hours after culture |
| WCCA | $1.6 \times 10^5$ | $6.0 \times 10^3$ | $7.6 \times 10^4$ | $1.08 \times 10^4$ | No growth | No growth |
| WCCT | $1.3 \times 10^4$ | $2.3 \times 10^2$ | $1.5 \times 10^4$ | $1.03 \times 10^3$ | No growth | No growth |
| WCHCL | $6.2 \times 10^5$ | $7.0 \times 10^3$ | 30 | 10 | No growth | No growth |
| Control (basal medium) | $2.2 \times 10^9$ | $1.4 \times 10^9$ | $3.6 \times 10^8$ | $4.6 \times 10^9$ | $5.5 \times 10^6$ | $1.0 \times 10^7$ |

24 hours after culturing, growth inhibition effects of the WCCT-1 medium (pH 6.27) on Gardnerella vaginalis (G. vaginalis) is similar to those of other media, WCCT-2 (pH 6.27) and WCCT-3 (pH 6.27) media. 48 hours after culturing, no colony grew in the WCCT-1 media.

TABLE 5

| Medium | 24 hours (/ml) after culture | 48 hours (/ml) after culture |
| --- | --- | --- |
| WCCT-1 | $6.0 \times 10^5$ | No growth |
| WCCT-2 | $4.2 \times 10^5$ | $2.0 \times 10^4$ |
| WCCT-3 | $4.2 \times 10^5$ | $3.3 \times 10^3$ |
| Control (basal medium) | $1.29 \times 10^8$ | $1.3 \times 10^5$ |

(2) Inhibition of Growth of Bacteroides fragilis (B. fragilis), Mobiluncus mulieris (M. mulieris), and Peptostreptococcus asaccharolyticus (P. asaccharolyticus)

The Wilkins-Chalgren anaerobe broth was used as a basal medium. A medium for each experiment was as follows.

TABLE 6

| | Control (basal medium) | WCCA | WCCT | WCHCL |
| --- | --- | --- | --- | --- |
| Citric acid monohydrate | — | 0.34% | 0.5% | — |
| Trisodium phosphate 12hydrate | — | — | 0.2% | — |
| Addition of 2 N hydrochloric acid (HCl) | X | X | X | ◯ |
| pH | 6.92 | 4.22 | 4.22 | 4.22 |

100 μl of a medium, which was sterilized and anaerobically cultured for 24 hours, for culturing three kinds of anaerobic strains was added to the screw cap tubes, followed by anaerobically culturing.

The number of Bacteroides fragilis (B. fragilis) at an early culture stage was $7.0\times10^8$/ml. The colony count was 13,000/ml 24 hours after culturing on WCCT medium and 230/ml 48 hours after culturing, which was remarkably reduced compared to the cases of other media (See FIG. 5A).

The colony count for Mobiluncus mulieris (M. mulieris) at an early culture stage was $3.2\times10^8$/ml. The colony count for Mobiluncus mulieris (M. mulieris) in the WCCA medium was $7.6\times10^4$/ml 24 hours after culturing and decreased to $1.08\times10^4$/ml 48 hours after culturing. In the case of the WCCT medium, the number of colonies was $1.5\times10^4$/ml 24 hours after culturing and $1.03\times10^3$/ml 48 hours after culturing, which was 1/10 in that of the WCCA medium. In the case of the WCHCL medium, the number of colonies was 30/ml 24 hours after culturing and greatly decreased to 10/ml 48 hours after culturing (See FIG. 5B).

The number of colonies from Peptostreptococcus asaccharolyticus (P. asaccharolyticus) at an early culture stage was $3.0\times10^6$/ml. Peptostreptococcus asaccharolyticus (P. asaccharolyticus) was respectively cultured in the WCCA, WCCT, and WCHCL media for 24 and 48 hours, but no colonies grew. On the other hand, in the case of a basal medium, the number of Peptostreptococcus asaccharolyticus (P. asaccharolyticus) was greatly increased 48 hours after culturing and thus the medium was turbid to the naked eye (See FIG. 5C).

(3) Growth Inhibition of Bacteria of the Present Invention

An MRS liquid medium (pH 5.7) was used as a basal medium. A medium for each experiment was as follows.

TABLE 8

| | Control (basal medium) | MRSCA | MRSCT | MRSHCL |
| --- | --- | --- | --- | --- |
| Citric acid monohydrate | — | 1.0% | 1.5% | — |
| Trisodium phosphate 12hydrate | — | — | 0.58% | — |

TABLE 8-continued

|  | Control (basal medium) | MRSCA | MRSCT | MRSHCL |
| --- | --- | --- | --- | --- |
| Addition of 5N hydrochloric acid (HCl) | X | X | X | ○ |
| pH | 5.7 | 4.2 | 4.2 | 4.2 |

Each of the media was aliquoted in an amount of 5 ml to a screw cap tube. The screw cap tube was inoculated with 100 μl of a medium containing each of *Steroidobacter denitrificans* (*S. denitrificans*) YH1 and *Lactobacillus crispatus* (*L. crispatus*) YH2 anaerobically cultured in sterilized basal media for 24 hours, followed by anaerobically culturing. 24 and 48 hours after culturing, each of media containing bacteria was spread on MRS agar according to a spread plate method (Unit: /ml).

TABLE 9

| | Strain | | | |
| --- | --- | --- | --- | --- |
| | *S. denitrificans* YH1 | | *L. crispatus* YH2 | |
| Medium | 24 hours after culture | 48 hours after culture | 24 hours after culture | 48 hours after culture |
| MRSCA | $6.8 \times 10^6$ | $1.25 \times 10^8$ | $2.5 \times 10^3$ | $2.6 \times 10^7$ |
| MRSCT | $6.7 \times 10^5$ | $1.8 \times 10^7$ | $3.5 \times 10^5$ | $4.6 \times 10^6$ |
| MRSHCL | $1.2 \times 10^8$ | $1.2 \times 10^8$ | $1.33 \times 10^6$ | $2.3 \times 10^7$ |
| Control (basal medium) | $1.9 \times 10^8$ | $2.0 \times 10^8$ | $3.0 \times 10^7$ | $7.0 \times 10^6$ |

Figure 6A:
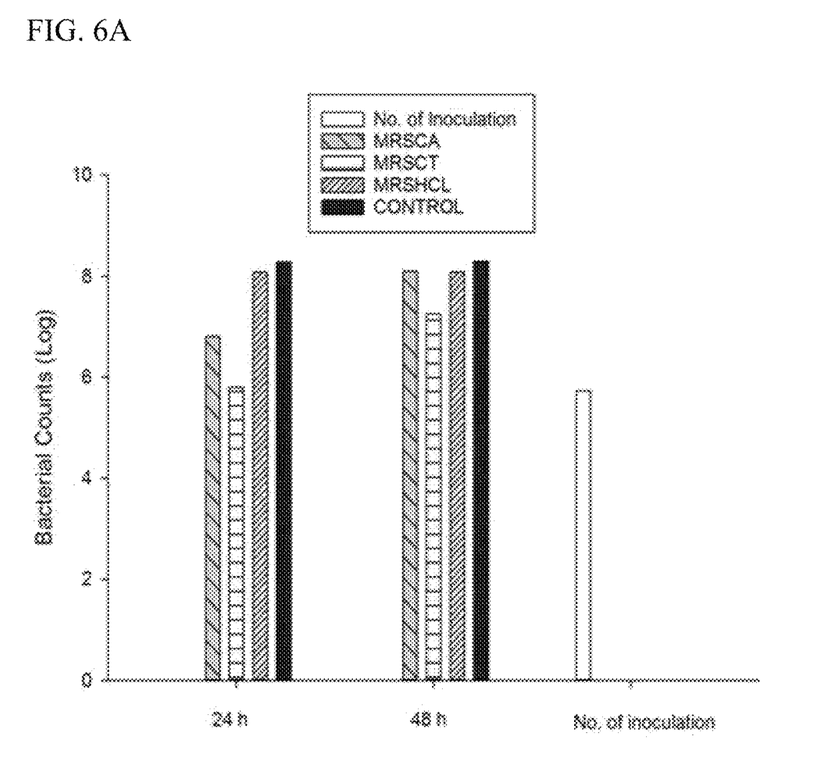
FIG. 6A illustrates a proliferation inhibition experiment result of *Steroidobacter denitrificans* YH1 with a mixed solution including citric acid and sodium phosphate tribasic.

The colony count for *Steroidobacter denitrificans* (*S. denitrificans*) YH1 at an early culture state was $3.4 \times 10^7$/ml. 24 hours after culturing, growth of colonies in the MRSCT medium (pH 4.2) was somewhat inhibited, compared to the cases of the MRSCA medium (pH 4.2) and the MRSHCL medium (pH 4.2), but, 48 hours after culture, bacterial growth rates in the media were not greatly different from that in the basal medium (pH 5.7) (See FIG. 6A).

Figure 6B:
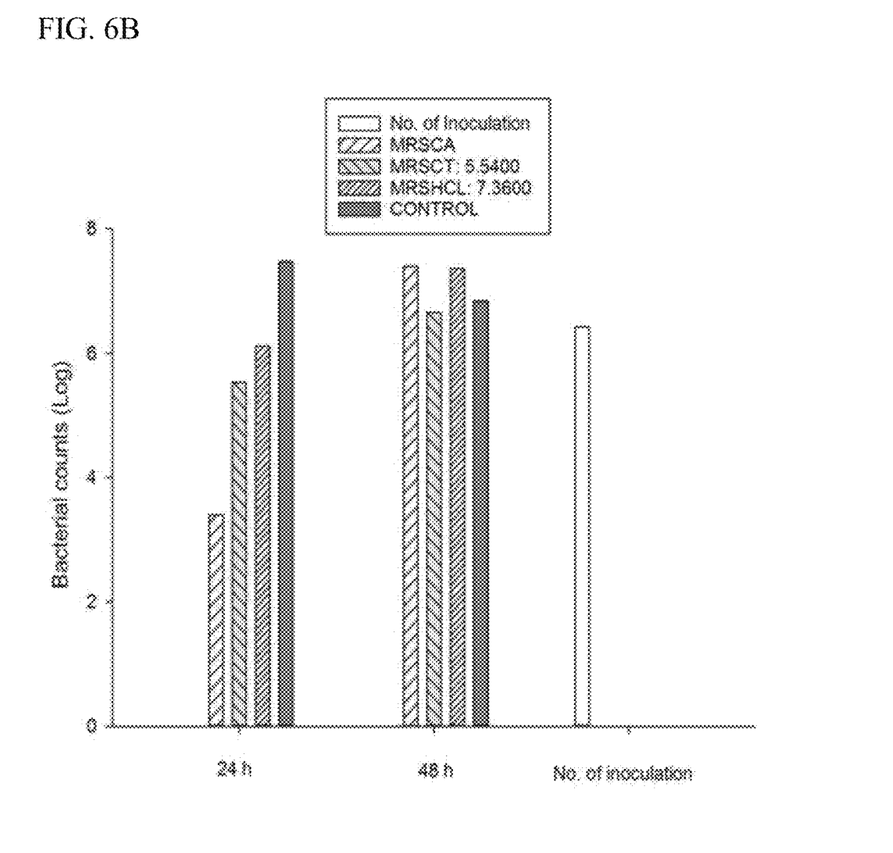
FIG. 6B illustrates a proliferation inhibition experiment result of *Lactobacillus crispatus* YH2 with a mixed solution including citric acid and sodium phosphate tribasic.

The colony count for *Lactobacillus crispatus* (*L. crispatus*) YH2 at an early culture stage was $2.7 \times 10^6$/ml. Although the strain was further satisfactorily cultured in the MRSCA medium 24 hours after culture, there was no great difference from the case of the MRSHCL medium. 48 hours after culturing, bacterial growth in the media was similar to that in the basal medium (See FIG. 6B).

6. Examination of Sensitivity of *Gardnerella vaginalis* (*G. vaginalis*) Strain and Strains of the Present Invention Bacteria to Antimicrobial Agents To screen antibiotics to which *Gardnerella vaginalis* (*G. vaginalis*) is sensitive, and are resistant to probiotics, antibiotics were tested using a disk diffusion assay.

Columbia agar containing a 5% human red blood cell solution was used as a media for *Gardnerella vaginalis* (*G. vaginalis*, ATCC 14018) and a MRS agar was used as a media for the strains of the present invention (*S. denitrificans* YH1 and *L. crispatus* YH2). As the antibiotic disk, a product manufactured by OXIOD was used.

The diameters of resultant inhibition zones were measured and are summarized in Table 10 (Unit: mm).

TABLE 10

|  | *G. vaginalis*, standard microorganism (ATCC 14018) | *S. denitrificans* YH1 | *L. crispatus* YH2 |
| --- | --- | --- | --- |
| Oxacillin | 0 | 0 | 0 |
| Ampicillin | 10 | 0 | 0 |
| Vancomycin | 40 | 35 | 35 |
| Carbenicillin | 40 | 35 | 35 |
| Gentamicin | 0 | 0 | 0 |
| Trimethoprim sulfamethoxazole | 0 | 0 | 0 |
| Imipenem | 40 | 30 | 25 |
| Penicillin G | 10 | 0 | 0 |
| Cefotaxime | 10 | 0 | 0 |

As described above, augmentin, metronidazole, and clindamycin were applied to a wild-type *Gardnerella vaginalis* (*G. vaginalis*) strain obtained from 33 patients suffering from bacterial vaginosis and a standard microorganism (ATCC 14018) and subjected to a test using a disk diffusion assay. Results are summarized in Table 11 below (Unit: mm).

TABLE 11

| *G. vaginalis* Strain No. | Diameter of inhibition zone per antibiotic | | | Biotype |
| --- | --- | --- | --- | --- |
| | Augmentin | Metronidazole | Clindamycin | |
| 14-1 | 60 | 27 | 50 | 1 |
| 14-2 | 33 | 0 | 60 | 5 |
| 14-3 | 40 | 40 | 55 | 4 |
| 14-4 | 45 | 35 | 50 | 6 |
| 14-5 | 40 | 35 | 45 | 4 |
| 14-6 | 60 | 32 | 45 | 1 |
| 14-7 | 40 | 0 | 60 | 5 |
| 14-8 | 50 | 0 | 50 | 3 |
| 14-9 | 35 | 0 | 50 | 2 |
| 14-10 | 35 | 0 | 55 | 3 |
| 14-11 | 60 | 0 | 60 | 2 |
| 14-12 | 35 | 0 | 50 | 5 |
| 14-13 | 30 | 0 | 55 | 5 |
| 14-14 | 40 | 35 | 50 | 4 |
| 14-15 | 45 | 0 | 60 | 5 |
| 14-16 | 45 | 25 | 60 | 8 |
| 14-17 | 35 | 0 | 55 | 5 |
| 14-19 | 40 | 0 | 55 | 5 |
| 14-20 | 60 | 0 | 50 | 7 |
| 14-21 | 50 | 30 | 50 | 8 |
| 14-23 | 35 | 33 | 55 | 8 |
| 14-24 | 50 | 20 | 50 | 8 |
| 14-25 | 60 | 25 | 55 | 5 |
| 14-26 | 50 | 0 | 65 | 5 |
| 14-27 | 50 | 0 | 55 | 4 |
| 14-28 | 30 | 0 | 60 | 5 |
| 14-29 | 40 | 0 | 65 | 5 |
| 14-30 | 55 | 0 | 65 | 5 |
| 14-32 | 50 | 0 | 60 | 5 |
| 14-33 | 45 | 0 | 55 | 7 |
| 14-34 | 40 | 0 | 60 | 5 |
| 14-36 | 40 | 0 | 60 | 5 |
| 14-37 | 60 | 20 | 60 | 1 |
| Standard microorganism ATCC 14018 | 60 | 0 | 55 | |
| Average ± SD | 44.9 ± 9.5 | — | 55.45 ± 5.5 | |

As results, metronidazole (50 μg/disc) did not show any inhibitory effects on 21 wild-type *Gardnerella vaginalis* (*G. vaginalis*) strains (64%), but showed inhibition zones of 20 to 40 mm for the remaining 12 strains (Table 11). With regard to Biotype 5, 14 of 15 strains (93%) were completely resistant. With regard to Biotypes 2, 3, 7 and 6, all strains were completely resistant. On the other hand, with regard to Biotypes 1, 4, 6, and 8, 11 of the 12 strains, except for one strain, showed inhibition zones of 20 to 40 mm. This data show that resistance to metronidazole is closely related to the biotypes. Meanwhile, clindamycin showed a wide inhibition zone of 55.45±5.5 mm on average and no strain was resistant thereto. Augmentin also showed a relatively wide inhibition zone of 44.9±9.5 mm on average and no strain was resistant thereto.

As described above, the strains of the present invention were applied with respect to the wild-type strains and tests using a disk diffusion assay were carried out. Results are summarized in Table 12 below (Unit: mm).

TABLE 12

| G. vaginalis strain No. | Biotype | Diameter of inhibition zone by S. denitrificans YH1 (mm) | G. vaginalis strain No. | Biotype | Diameter of inhibition zone by L. crispatus YH2 |
|---|---|---|---|---|---|
| 14-2 | 5 | 40 | 14-12 | 5 | 18 |
| 14-7 | 5 | 46 | 14-13 | 5 | 13 |
| 14-9 | 2 | 27 | 14-15 | 5 | 22 |
| 14-12 | 5 | 20 | 14-17 | 5 | 12 |
| 14-13 | 5 | 13 | 14-19 | 5 | 27 |
| 14-14 | 4 | 23 | 14-20 | 7 | 26 |
| 14-15 | 5 | 25 | 14-25 | 5 | 42 |
| 14-17 | 5 | 16 | 14-26 | 5 | 25 |
| 14-19 | 5 | 31 | 14-28 | 5 | 14 |
| 14-20 | 7 | 34 | 14-29 | 5 | 12 |
| 14-25 | 5 | 36 | 14-30 | 5 | 32 |
| 14-28 | 5 | 20 | 14-32 | 5 | 31 |
| 14-29 | 5 | 18 | 14-33 | 7 | 21 |
| 14-36 | 5 | 38 | 14-36 | 5 | 30 |
| 14-37 | 1 | 24 | 14-37 | 1 | 33 |
| Average ± SD | | 27.4 ± 9.7 | Average ± SD | | 23.9 ± 8.97 |

As experimental results, an average diameter of inhibition zones was 27.4±9.7 mm in the case of *Steroidobacter denitrificans* (*S. denitrificans*) YH1 and 23.9±8.97 mm in *Lactobacillus crispatus* (*L. crispatus*) YH2. In addition, various inhibition zones were exhibited in the same biotypes, thereby demonstrating that the kinds of the biotypes were not correlated with inhibitory effects of the probiotics.

Taking the data together, it can be predicted that the therapeutic effect is maximized and settlement of the two probiotic types in the interior of the vagina is stably accomplished when, since the wild-type *Gardnerella vaginalis* (*G. vaginalis*) strains have strong resistance to metronidazole, pretreatment with clindamycin, to which there is no resistance, is conducted and then other formulations, other than amoxicillin, are applied.

7. Preparation of Composition for Treatment

Citric acid was added to the Man-Rogosa-Sharpe (MRS) liquid medium in an amount of 1 to 1.5%. Sodium phosphate tribasic was added thereto in an amount of 0.5 to 0.8% and the concentration of hydrogen ions was adjusted to about pH 4.0 to 4.5. *Steroidobacter denitrificans* (*S. denitrificans*) YH1 isolated through centrifugation was added thereto in a number of $1.0 \times 10^7$ to $10^9$/ml. *Lactobacillus crispatus* (*L. crispatus*) YH2 was mixed therewith in a number of $1.0 \times 10^7$ to $10^9$/ml. A resultant mixture was contained in a glass bottle for freeze-drying. The glass bottle was equipped with a rubber stopper and moisture was removed therefrom using a freeze-dryer, followed by vacuum packing.

8. Administration of Treatment Composition

Before use, 2 ml of distilled water was injected to the vacuum-packed composition with a syringe, followed by shaking and re-suspending. Subsequently, the rubber stopper was removed from the bottle and then the suspension was suctioned into a disposable dropper, and subsequently, deeply deposited into the interior of the vagina of a woman. The frequency of administration depends upon the patients and may be about two to five times a week.

As described above, the present invention provides a lactic acid bacteria-containing composition for treating vaginosis, the composition exhibiting a superior therapeutic effect for bacterial vaginosis in women. In particular, the strains used in the present invention become main bacteria (normal flora) in the environment of the vagina of a patient suffering from bacterial vaginosis and inhibit the proliferation of causative bacteria of the bacterial vaginosis. In addition, when a buffer containing citric acid and sodium phosphate tribasic is included, the growth of causative bacteria of vaginosis is directly inhibited and the survival of the strains of the present invention is guaranteed, thereby further increasing the pathogen inhibition capability of the bacteria strains. Accordingly, the present invention can restore a bacterial ecosystem in the vagina of a patient suffering from recurrent bacterial or atrophic vaginosis to an original healthy state and greatly lower a recurrence rate of an illness.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A composition for treating vaginosis, comprising:
   *Steroidobacter denitrificans* YH1 (KCTC18345P) and *Lactobacillus crispatus* YH2 (KCTC18346P) strains; and
   at least one buffer selected from the group consisting of sodium phosphate monobasic, sodium phosphate dibasic, sodium phosphate tribasic, citric acid, sodium citrate, phosphoric acid, hydrochloric acid, sodium hydroxide, sodium pyrophosphate, and pyrophosphate.

2. The composition according to claim 1, wherein the buffer further comprises sodium phosphate tribasic and citric acid.

3. The composition according to claim 1, wherein the buffer is comprised in an amount of 0.01 to 10% (W/V).

4. The composition according to claim 1, wherein the composition has a pH of 2 to 7.

5. The composition according to claim 1, wherein the strains are comprised in a number of $1.0 \times 10^7$ to $10^9$ cells/ml of *Steroidobacter denitrificans* YH1 (KCTC18345P) and $1.0 \times 10^7$ to $10^9$ cells/ml of *Lactobacillus crispatus* YH2 (KCTC18346P) in the composition.

6. The composition according to claim 1, wherein a ratio of the number of *Lactobacillus crispatus* (*Lactobacillus crispatus*) YH2 (KCTC18346P) to the number of the *Steroidobacter denitrificans* YH1 (KCTC18345P) is 1:100 to 100:1.

7. The composition according to claim 1, wherein the composition reduces, eliminates, and/or inactivates pathogens selected from the group comprising *Gardnerella vaginalis, Trichomonas vaginalis, Neisseria gonorrhoeae, Streptococcus, Staphylococcus, Escherichia coli, Peptostreptococcus* spp., *Mobiluncus* spp., *Bacteroides* spp., *Prevotella* spp., *Peptococcus* spp., and *Mycoplasma hominis*.

* * * * *